United States Patent
Cramer et al.

(10) Patent No.: US 6,767,449 B2
(45) Date of Patent: Jul. 27, 2004

(54) METHOD FOR OPERATING A SENSOR FOR DETERMINING THE CONCENTRATION OF OXIDIZING GASES IN GAS MIXTURES

(75) Inventors: Berndt Cramer, Leonberg (DE); Bernd Schumann, Rutesheim (DE)

(73) Assignee: Robert Bosch GmbH, Stuttgart (DE)

(*) Notice: Subject to any disclaimer, the term of this patent is extended or adjusted under 35 U.S.C. 154(b) by 233 days.

(21) Appl. No.: 09/914,208

(22) PCT Filed: Dec. 20, 2000

(86) PCT No.: PCT/DE00/04550

§ 371 (c)(1),
(2), (4) Date: Nov. 30, 2001

(87) PCT Pub. No.: WO01/48467

PCT Pub. Date: Jul. 5, 2001

(65) Prior Publication Data

US 2002/0157452 A1 Oct. 31, 2002

(30) Foreign Application Priority Data

Dec. 23, 1999 (DE) .......................... 199 62 912

(51) Int. Cl.[7] ............................................ G01N 27/419
(52) U.S. Cl. .................... 205/781; 205/784.5; 204/406; 204/425
(58) Field of Search ................. 205/781, 784, 205/784.5; 204/425, 427, 406; 73/23.31

(56) References Cited

U.S. PATENT DOCUMENTS 6,383,354 B1 * 5/2002 Kurokawa et al. .......... 204/425

FOREIGN PATENT DOCUMENTS

| DE | 199 07 946 | 9/2000 |
|----|------------|--------|
| EP | 0 791 826  | 8/1997 |
| EP | 0 798 555  | 10/1997 |
| EP | 0 859 232  | 8/1998 |
| EP | 0 892 265  | 1/1999 |
| EP | 0 937 980  | 8/1999 |
| FR | 2 794 863  | 12/2000 |

* cited by examiner

Primary Examiner—Kaj K. Olsen
(74) Attorney, Agent, or Firm—Walter Ottesen

(57) ABSTRACT

Method for operating a sensor for determining the concentration of oxidizing gases in gas mixtures, especially of the nitrogen oxide concentration in exhaust gases of internal combustion engines, wherein the sensor includes: at least one chamber (1; 2) mounted in a solid state electrolyte (20), the chamber being connected to the gas mixture via a first diffusion barrier (4); a second chamber (3) arranged in the solid state electrolyte (20) and the chamber having a pregivable constant oxygen partial pressure; on the solid state electrolyte, an oxygen pump electrode (9) subjected to the exhaust gas; a further oxygen pump electrode (7; 8) as well as an NO pump electrode (10) in the at least one chamber (1; 2); and an oxygen reference electrode (6) arranged in the second chamber (3); and at least a voltage is made available at the electrodes and at least a pump current is evaluated as a measurement signal. The method is characterized in that the voltages (U_IPE; U_O2; U_NO), which are applied to the electrodes, are changed in dependence upon the currents, which flow in the electrode feed lines and/or between the electrodes (6; 7; 8; 9; 10), during operation of the sensor in such a manner that the voltages correspond to pregivable desired values, these voltages being applied to the electrodes (6; 7; 8; 9; 10) in the interior of the sensor.

4 Claims, 4 Drawing Sheets

US 6,767,449 B2

METHOD FOR OPERATING A SENSOR FOR DETERMINING THE CONCENTRATION OF OXIDIZING GASES IN GAS MIXTURES

FIELD OF THE INVENTION

The invention relates to a method for operating a sensor for determining the concentration of oxidizing gases, especially for determining the nitrogen oxide concentration in exhaust gases of internal combustion engines.

BACKGROUND OF THE INVENTION

Such a sensor is presented, for example, in U.S. Pat. No. 5,942,190.

Electrical fields and electrical currents arise between the individual electrodes and between the electrodes and the heater which cause the measuring result to be incorrect. This occurs because all electrodes of such a sensor are conductively is connected to the solid state electrolyte and the insulation layer of the heater has a finite resistance and, accordingly, all electrodes are connected to each other via electrically conductive structures and are connected at high resistance to the heater.

SUMMARY OF THE INVENTION

The method of the invention offers the advantage that the measuring errors can be eliminated by active compensation or at least can be minimized. The measurement errors arise because of the mutual coupling of the electrodes via electrical fields and currents in the solid state electrolyte as well as by the voltage drops across the feed line resistances. It is possible to precisely adjust the voltages on the electrodes without voltages on the electrodes being made incorrect by erroneous voltage drops on the electrode feed lines. This is made possible by changing the voltages, which are applied to the electrodes in accordance with function, in dependence upon the currents which flow in the electrode feed lines and/or between the electrodes. It is especially advantageous that the adjustment is independent of the current intensity with which the individual electrodes are charged.

An advantageous embodiment provides that one adds voltages to the voltages applied to the electrodes. The voltages added correspond to a feedback of voltage components weighted with factors and these voltage components are proportional to the currents. Furthermore, the sliding mean values of the voltages and/or their derivation of higher order and/or their sliding mean values or linear combinations thereof can be fed back. These voltages are proportional to the currents and the mean values are formed by means of known electric circuit elements. In this way, it is also possible to eliminate capacitive couplings.

The adjustment of the voltage on the electrodes takes place in this case advantageously by changing these factors. These factors are increased until the system starts to oscillate because of the feedback. The oscillation arises when the fed back factor is $\geq 1$ in magnitude and, at the same time, the phase is greater than or equal to 180°. Then, the factors are reduced slightly but only so far that just no oscillation occurs anymore. In this way, almost all voltage drops, which arise at the electrode feed lines, as well as the voltage drops which arise because of a fictive resistance network within the solid state electrolytes, can be compensated.

BRIEF DESCRIPTION OF THE DRAWING

Further advantages and features of the invention are the subject matter of the following description as well as the schematic representation of an embodiment of the invention.

The drawings show.

DESCRIPTION OF THE PREFERRED EMBODIMENTS OF THE INVENTION

Figure 1:
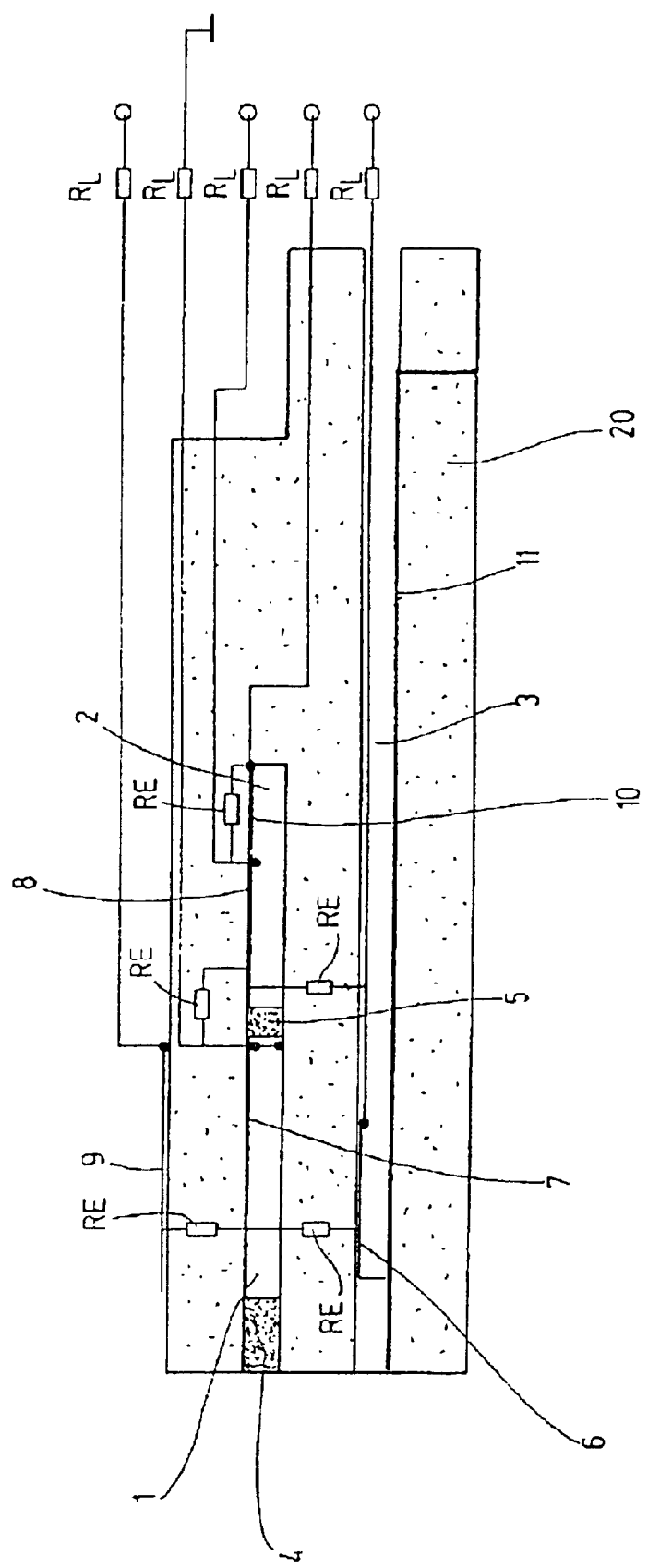
FIG. 1 is a schematic section view through a sensor, which is known from the state of the art, for determining oxides in gas mixtures.

An NOx double chamber sensor is shown in FIG. 1 and includes five electrodes, namely: an oxygen pump electrode 9 subjected to the exhaust gas; an oxygen pump electrode 7 mounted in a first chamber and essentially lying opposite to the oxygen pump electrode 9 subjected to the exhaust gas; an oxygen pump electrode 8 arranged in a second chamber 2; and NO pump electrode 10 mounted likewise in the second chamber 2; and, an air reference electrode 6 mounted in a third chamber 3.

The first chamber 1 is connected via a diffusion barrier 4 to the exhaust gas, the second chamber 2 is connected to the first chamber via a further diffusion barrier 5.

The third chamber 3 is connected to the atmosphere via a channel.

The oxygen pump electrodes 7 and 8 pump oxygen away from the first chamber 1 or from the second chamber 2. The external pump electrode 9 functions as a counter electrode.

Nitrogen oxides are pumped away by the NO pump electrode 10. All electrodes are arranged on an ion-conducting solid state electrolyte 20 which, for example, can be made of zirconium oxide and are electrically conductively connected therewith.

An insulated heater 11 is provided in order to heat up the sensor to the necessary operating temperature.

Figure 2:
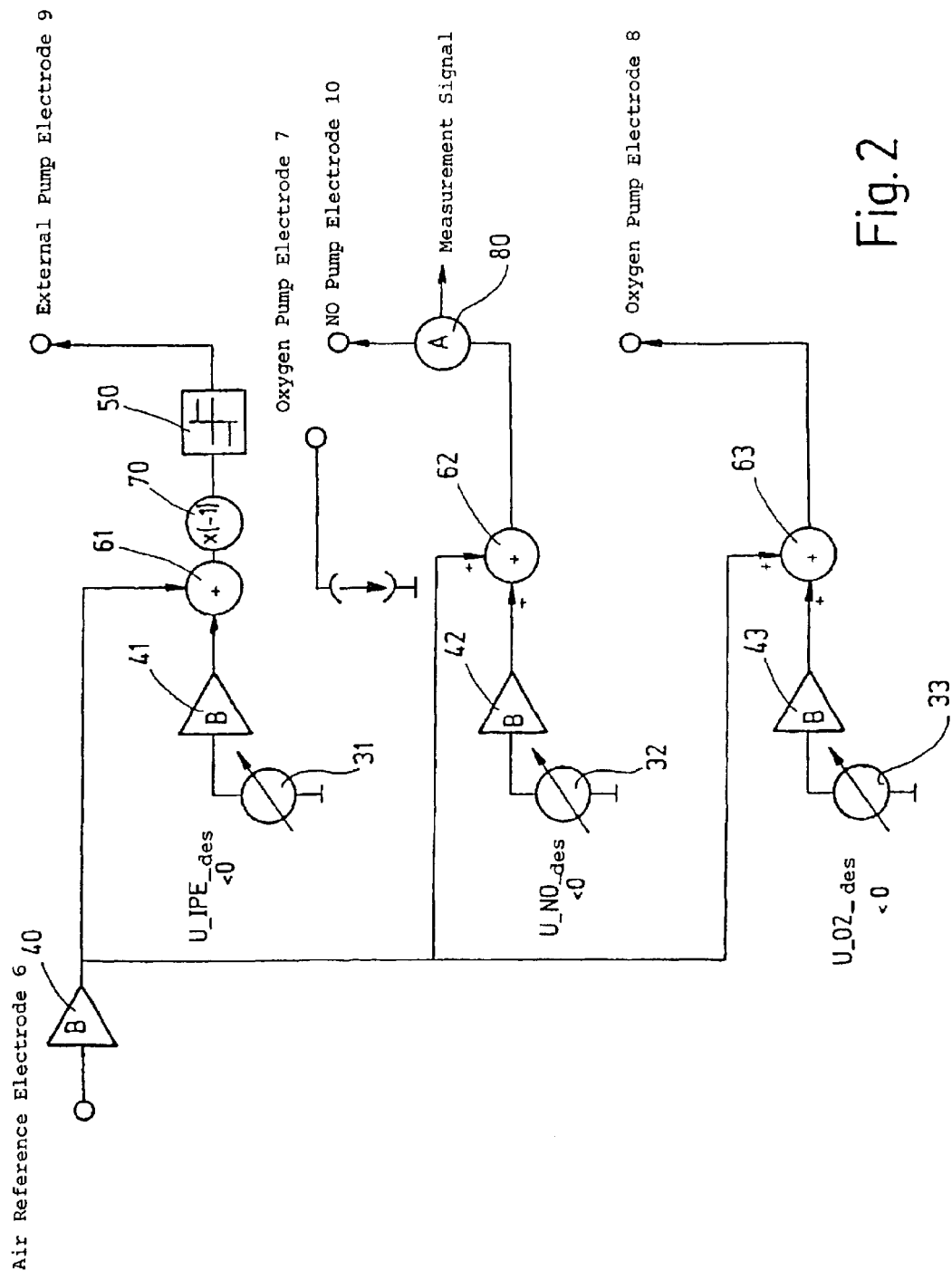
FIG. 2 shows schematically a circuit arrangement, which is known from the state of the art, for a sensor shown in FIG. 1.

An evaluation circuit functions to operate the sensor and this circuit makes various electrical voltages available and obtains the measurement signal from a current measurement. A block circuit diagram of such a circuit, which is known from the state of the art, is shown schematically in FIG. 2. The three voltages for the oxygen pump electrodes (7, 8) as well as for the NO pump electrode 10 are generated by voltage references 31, 32, 33 and drivers 41, 42, 43 and are shifted by the potential of the air reference. The oxygen pump electrodes 7, 8 lie in the first chamber 1 and in the second chamber 2. For the above, the voltage, which is outputted by the driver 40, is added to or subtracted from the voltage outputted by drivers 41, 42, 43 in adding elements 61, 62, 63 in a manner known per se. The potential of the outer pump electrode 9 is adjusted via a two-point controller 50 until the voltage difference between the oxygen pump electrode 7 and the air reference electrode 6 corresponds to a pregivable desired value. The other electrode potentials are adjusted directly. The NO pump current can be measured via a current-voltage converter 80 known per se and be outputted as a measurement signal.

All electrodes are conductively connected to the solid state electrolyte 20 and the insulation layer of the heater 11 has a finite resistance. For this reason, all electrodes are connected to each other via a conductance network and are connected at high ohmage to the heater 11. The numerically largest conductances are shown in FIG. 1 schematically by the resistances $R_E$. Likewise, feed conductances of the conductive paths to the electrodes are present which are likewise shown schematically in FIG. 1 by resistances $R_L$.

The basic idea of the invention is to make possible the adjustment of the required voltages directly at the electrodes without the voltage drop across the feed line resistors $R_L$ or the mutual coupling of the electrodes via the resistances $R_E$ making these electrode voltages incorrect.

Figure 3:
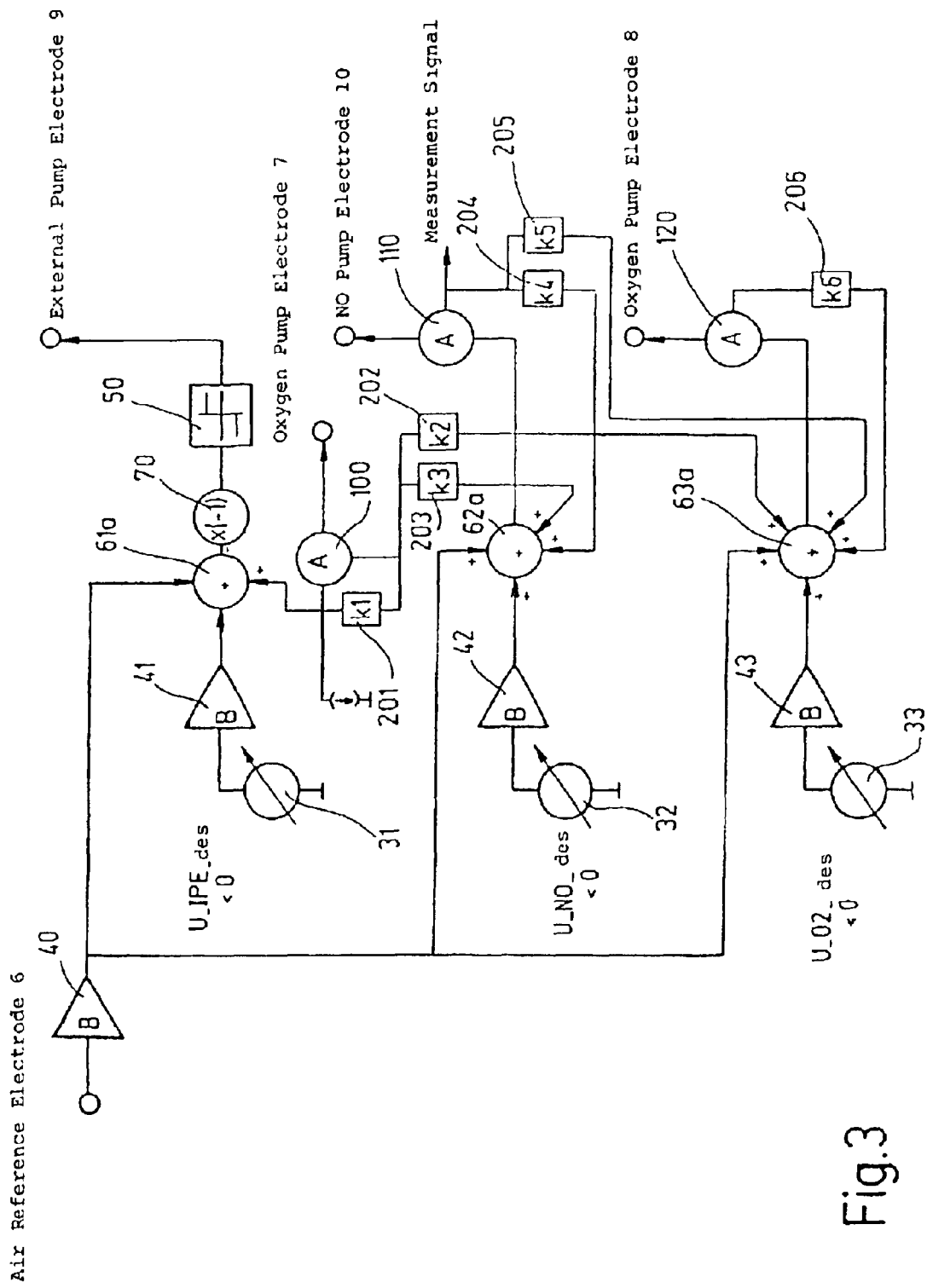
FIG. 3 is an embodiment of a circuit arrangement for a sensor shown in FIG. 1 which is suitable for carrying out the method of the invention; and, FIG. 4 schematically shows the coupling of the voltages/ currents in matrix form which lie across the electrodes of a sensor shown in FIG. 1.

This is solved by a method for operating a sensor which is explained in combination with a circuit shown in FIG. 3. In the circuit shown in FIG. 3, those elements which are identical to those in the circuit shown in FIG. 2 have the same reference numerals so that, with reference to their description, reference is made to the presentation made to the circuit shown in FIG. 2. The circuit shown in FIG. 3 differs from the circuit shown in FIG. 2 in that circuit arrangements are provided by which the voltages U_IPE, U_NO, U_O2, which are applied to the electrodes 7, 8, 10, 9, are changeable in dependence upon the currents flowing in the measurement lines and/or between the electrodes. These circuit arrangements include current/voltage converters 100, 110, 120 and circuit elements (compensation branches) 201, 202, 203, 204, 205, 206 which are weighted with compensation factors K1, K2, K3, K4, K5, K6 in such a manner that a component, which is proportional to the currents, is so fed back to the electrodes that the components, which are coupled in via the solid state electrolyte 20, and the feed losses are compensated. With a feedback of this kind, the potentials of the electrodes, which can be measured on the feed lines, are dependent upon the currents in the solid state electrolyte 20 and in the feed lines. The currents in the solid state electrolytes 20 are not accessible to a measurement but result at every location from the linear combination of currents in the feed lines. The total system is viewed as being linearly electrical. Because of the linear combination of the currents at each location, one obtains voltages also at the locations of the electrodes which are linearly dependent upon the feed line currents. The feedback takes place in such a manner that first the factor K1 is increased stepwise until there is an oscillation because of the feedback. Then, the factor K1 is again reduced slightly until just no oscillation occurs. Correspondingly, and if still necessary, one can proceed with the additional factors K2 to K5. In this way, it is ensured that practically all disturbing influences because of the electrode feed lines and because of the resistances between the electrodes are eliminated. These resistances are present in the solid state electrolyte 20 and are disturbing. Additionally, the sliding mean values of the voltages formed by means of electrical circuit elements and/or their derivatives of higher order and/or their sliding mean values or linear combinations thereof can be fed back. The voltages are proportional to the current. In this way, not only ohmic but also capacitive couplings are eliminated.

Figure 4:
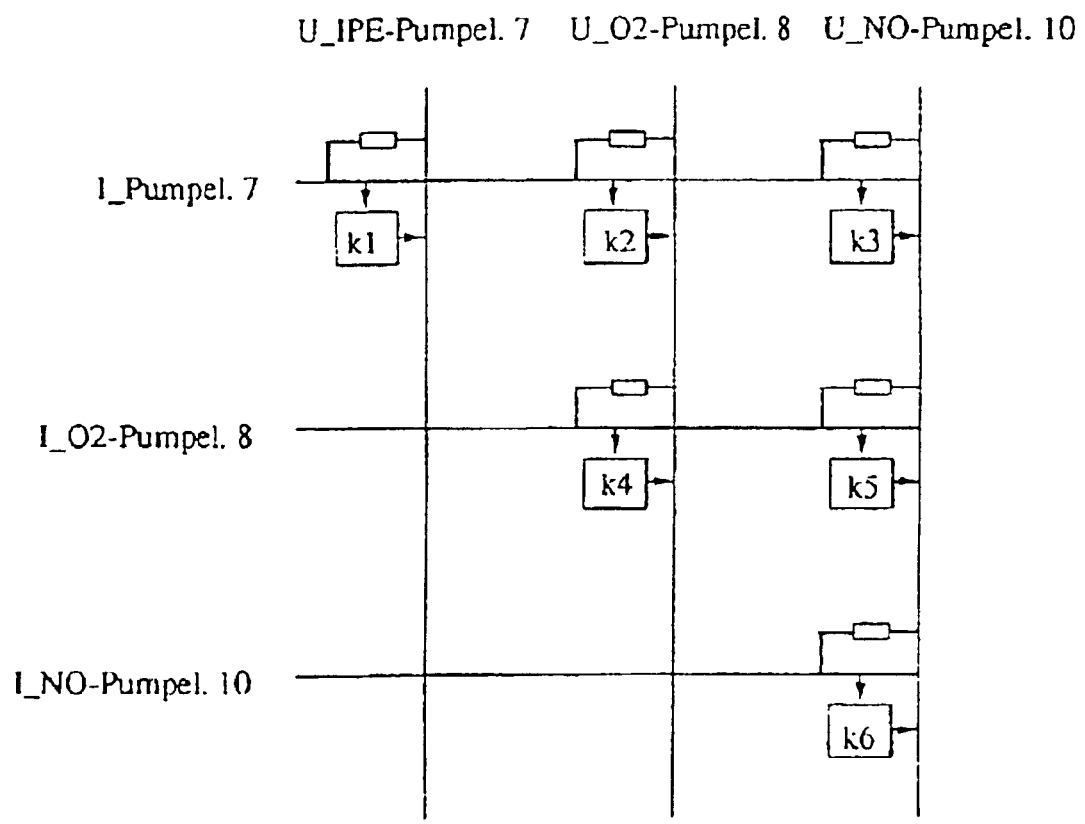

FIG. 4 shows schematically the coupling matrix. The lines are formed by the currents of the electrodes I_pump electrode 7, I_O2 pump electrode 8 and I_NO pump electrode 10. The current of the inner oxygen pump electrode I_pump electrode 7 is relatively large compared to the other two and has therefore significant influence on the electrode voltages U_IPE or on the pump electrode 7, U_O2 on the pump electrode 8 and U_NO on the pump electrode 10. The spatial closeness of the oxygen pump electrode 8 and the NO pump electrode 10 to each other in the second chamber 2 leads to a pronounced coupling. The components of the main diagonal of the coupling matrix result from the feed line resistances. It is sufficient to consider the compensation factors K2, K3, K5 and K1, K4, K6 arranged on one side of the main diagonal.

What is claimed is:

1. A method for operating a sensor for determining the concentration of oxidizing gases in gas mixtures and especially for determining the nitrogen oxide concentration in exhaust gases of an internal combustion engine, the sensor including: a first chamber disposed in a solid state electrolyte, the chamber being connected to the gas mixture via a first diffusion barrier; a second chamber arranged in the solid state electrolyte and said second chamber having a pregivable constant oxygen partial pressure; an oxygen pump electrode subjected to the exhaust gas on the solid state electrolyte; a further oxygen pump electrode and a nitrogen oxide pump electrode in said first chamber; and, an oxygen reference electrode arranged said second chamber; the method comprising the steps of:

applying voltages (U-IPE; U-O2; U-NO) to the oxygen pump electrode, further oxygen pump electrode and nitrogen oxide pump electrode, respectively, thereby generating respective pump currents;

measuring one of said pump currents and outputting said one pump current as a measurement signal; and, changing said voltages (U-IPE, U-O2; U-NO), which are applied to the pump electrodes, in dependence upon factors which correspond to the characteristic resistances or conductivities between said electrodes, during operation of the sensor in such a manner that the voltages correspond to predetermined desired values in the interior of said sensor.

2. The method of claim 1, wherein said voltages (U_IPE; U_O2; U_NO) are changed by adding voltages thereto which correspond to a feedback of voltage components weighted with factors (K1, K2, K3, K4, K5 and/or K6) which voltage components are proportional to said factors.

3. The method of claim 1, wherein at least one of the factors (K1, K2, K3, K4, K5, K6) is increased so long until an oscillation of said sensor occurs because of the feedback and that one slightly reduces this factor (K1, K2, K3, K4, K5, K6) by an amount determined experimentally so that just no oscillation occurs anymore.

4. A method for operating a sensor for determining the concentration of oxidizing gases in gas mixtures and especially for determining the nitrogen oxide concentration in exhaust gases of an internal combustion engine, the sensor including: a first chamber disposed in a solid state electrolyte, the chamber being connected to the gas mixture via a first diffusion barrier; a second chamber arranged in the solid state electrolyte and said second chamber having a pregivable constant oxygen partial pressure; an oxygen pump electrode subjected to the exhaust gas on the solid state electrolyte; a further oxygen pump electrode and a nitrogen oxide pump electrode in said first chamber; and, an oxygen reference electrode arranged in said second chamber; the method comprising the steps of:

applying voltages (U-IPE; U-O2; U-NO) to the oxygen pump electrode, further oxygen pump electrode and nitrogen oxide pump electrode, respectively, thereby generating respective pump currents;

measuring one of said pump currents and outputting said one pump current as a measurement signal;

changing said voltages (U-IPE, U-O2; U-NO), which are applied to the pump electrodes, in dependence upon factors which correspond to the characteristic resistances or conductivities between said electrodes, during operation of the sensor in such a manner that the voltages correspond to predetermined desired values in the interior of said sensor, and, wherein said voltages (U-IPE; U-O2; U-NO) are changed by adding voltages thereto which correspond to a feedback of voltage components weighted with factors (K1, K2, K3, K4, K5, and/or K6) which voltage components are proportional the sliding mean values of the voltages, which are proportional to said factors and which are formed by means of electric circuit elements and/or the derivatives of higher order and/or their sliding mean values or linear combinations thereof.

* * * * *

UNITED STATES PATENT AND TRADEMARK OFFICE
CERTIFICATE OF CORRECTION

PATENT NO. : 6,767,449 B2
DATED : July 27, 2004
INVENTOR(S) : Berndt Cramer and Bernd Schumann It is certified that error appears in the above-identified patent and that said Letters Patent is hereby corrected as shown below:

Column 4,
Line 17, insert -- in -- after "arranged".
Line 63, delete "(U-IPE, U-O2; U-NO)" and substitute -- (U-IPE; U-O2; U-NO) -- therefor.

Column 5,
Line 2, delete "sensor," and substitute -- sensor; -- therefor.
Line 7, insert -- to -- after "proportional".

Signed and Sealed this

Twenty-first Day of December, 2004

JON W. DUDAS
*Director of the United States Patent and Trademark Office*